US00PP36079P2

(12) United States Plant Patent
Aguilar Morán

(10) Patent No.: US PP36,079 P2
(45) Date of Patent: Aug. 27, 2024

(54) DESSERT BANANA PLANT NAMED "SH-4199"

(50) Latin Name: *Musa acuminata*
Varietal Denomination: SH-4199

(71) Applicant: Fundación Hondureña de Investigación Agrícola (FHIA), San Pedro Sula (HN)

(72) Inventor: Juan Fernando Aguilar Morán, La Lima (HN)

(73) Assignee: Fundación Hondureña de Investigación Agrícola (FHIA) (HN)

( * ) Notice: Subject to any disclaimer, the term of this patent is extended or adjusted under 35 U.S.C. 154(b) by 0 days.

(21) Appl. No.: 18/469,772

(22) Filed: Sep. 19, 2023

(51) Int. Cl.
*A01H 5/08* (2018.01)

(52) U.S. Cl.
USPC ..... Plt./160

(58) Field of Classification Search
USPC ..... Plt./160
CPC ..... A01H 6/00; A01H 5/08
See application file for complete search history.

*Primary Examiner* — Keith O. Robinson
(74) *Attorney, Agent, or Firm* — Garvey, Smith & Nehrbass, Patent Attorneys, L.L.C.; Seth M. Nehrbass; Fabian M. Nehrbass

(57) ABSTRACT

'SH-4199' is a hybrid dessert banana variety that has a dwarf stature, is resistant to black Sigatoka, and produces high-quality fruit.

6 Drawing Sheets

Latin name of the genus and species of the plant claimed: This tetraploid plant has only *Musa acuminata* in its pedigree. This tetraploid hybrid is the product of an inter-specific cross between one diploid (AA) and two triploid (AAA) cultivars. Its Latin name is *M. acuminata* group (AAAA), representing four genomes of the *M. acuminata.*

Variety denomination: 'SH-4199'.

STATEMENT REGARDING FEDERALLY SPONSORED RESEARCH OR DEVELOPMENT

Not applicable.

BACKGROUND OF THE INVENTION

This invention relates to a new and distinctive hybrid banana plant variety named 'SH-4199'. This new hybrid variety was the result of a field cross performed in 2016 in La Lima Cortés, Honduras, between 'SH-4168' x 'SH-3142' (Both unpatented). The female parent 'SH-4168' is a medium triploid plant (AAA) "Cavendish type" tolerant to Black Sigatoka leaf spot disease (*Mycosphaerella fijiensis*), developed from accessions and breeding lines a germplasm bank. The pedigree of 'SH-4168' is 'ITC-570' ('Williams') x 'Novak', both belonging to the Cavendish group.

The male parent, 'SH-3142', is diploid (AA), resistant to burrowing nematodes (*Radopholus similis*), Sigatoka leaf disease (*Mycosphaerella fijiensis*), and *Fusarium* wilt (*Fusarium oxysporum f.* sp. *cubense* Race 1 and 4). The pedigree of 'SH-3142' is 'AVP-357' and 'II-30'→'III-133' x 'SH-77'→'SH-1734' x 'II-155'→'SH-3142'. 'AVP-357' is a *Musa acuminata* subsp. *malaccensis* diploid (AA) from the two original parental lines, and the 'II-30' is a *Musa acuminata* subsp. *errans* diploid (AA).

'SH-4199' was selected in 2018 from several first-generation seedlings from the cross between 'SH-4168' and 'SH-3142'. It was chosen as a tetraploid hybrid maintaining the "Cavendish type" stature and taste of its female parental line and producing bunches of 20 kilograms with fruits of the same quality as the mother 'SH-4168'. Furthermore, it presents the black Sigatoka leaf spot disease (*Mycosphaerella fijiensis*) resistance of his 'SH-3142' male parental line. 'SH-4199' was asexually reproduced by corms by the breeder in La Lima Cortes, Honduras. All plants and fruit run true to the initially selected plant and are identical in all aspects.

The hybrid 'SH-4199' has many similarities with its mother, 'SH-4168'. These similarities include the plant's size, the shape of the cluster, the distribution of the leaves, the shape of the fingers, and the flavor. However, 'SH-4199' is more resistant to black Sigatoka (*Mycosphaerella fijiensis*) than 'SH-4168'. It is possible that 'SH-4199' inherited this resistance from its parent 'SH-3142', which is a tall plant with a large bunch and an unpleasant flavor and is very different from 'SH-4199'. 'SH-4199' differs from commercial varieties such as 'Grand Naine' or 'Williams' in fruit taste and bunch size. Compared to 'Grand Naine' or 'Williams', 'SH-4199' may not have the same commercial value, but it has the potential to contribute to the development of better varieties.

BRIEF SUMMARY OF THE INVENTION

'SH-4199' is a hybrid dessert banana variety with a dwarf stature, is resistant to black Sigatoka, and produces high-quality fruit.

BRIEF DESCRIPTION OF THE PHOTOGRAPHS

The figures describe the characteristics of the 'SH-4199' hybrid banana variety. The color shown in the photographs is as nearly accurate as reasonably possible in this type's color representation.

FIG. 1 shows the typical appearance of a plant at ten (10) months old;

FIG. 2A-B show blotches of the petiole base (A) and a petiole canal (B);

FIG. 3A-C shows the shape of a leaf blade base (A) and leaf upper (B) and lower (C) surfaces;

FIG. 4A-B shows water suckers (A) and leaves without blotches (B);

Figure 1:
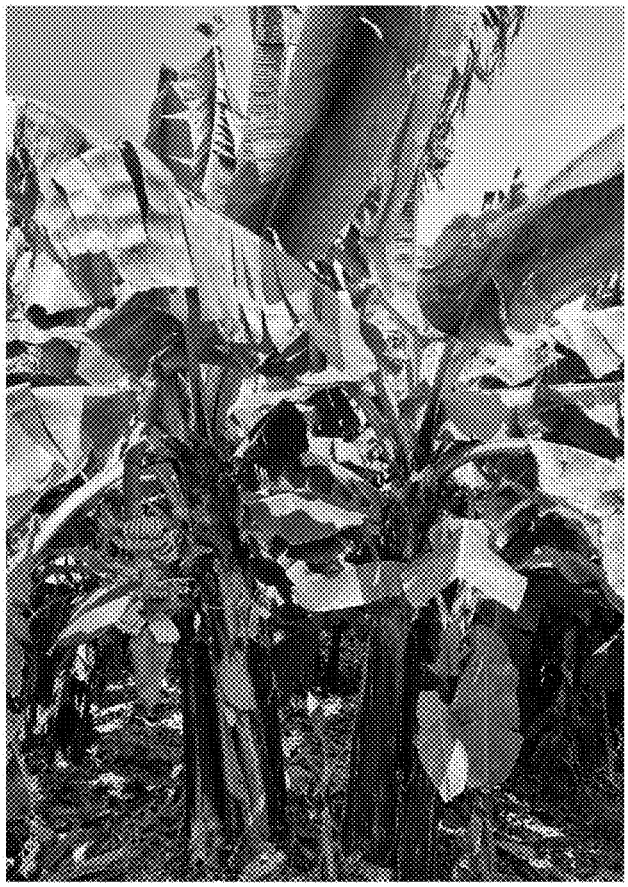
Figures 2A, 2B:
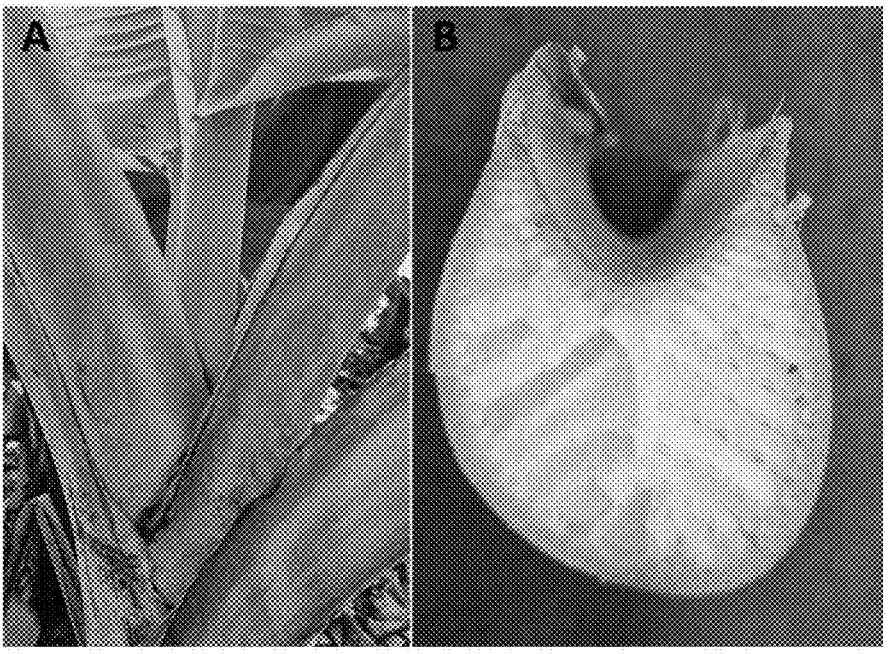
Figure 5:
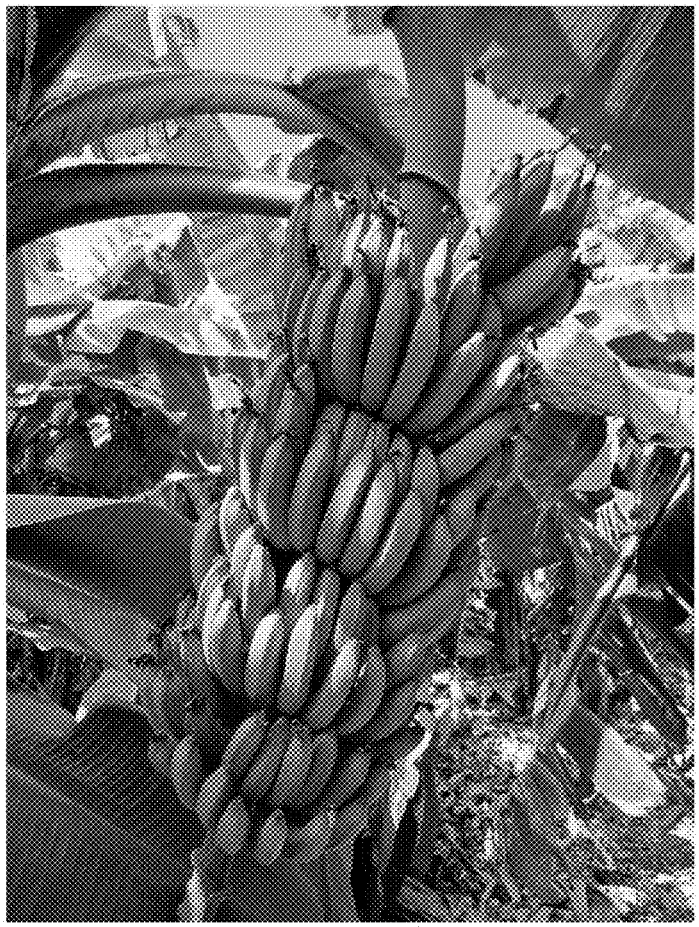
FIG. 5 shows a typical fruit bunch.
Figure 6:
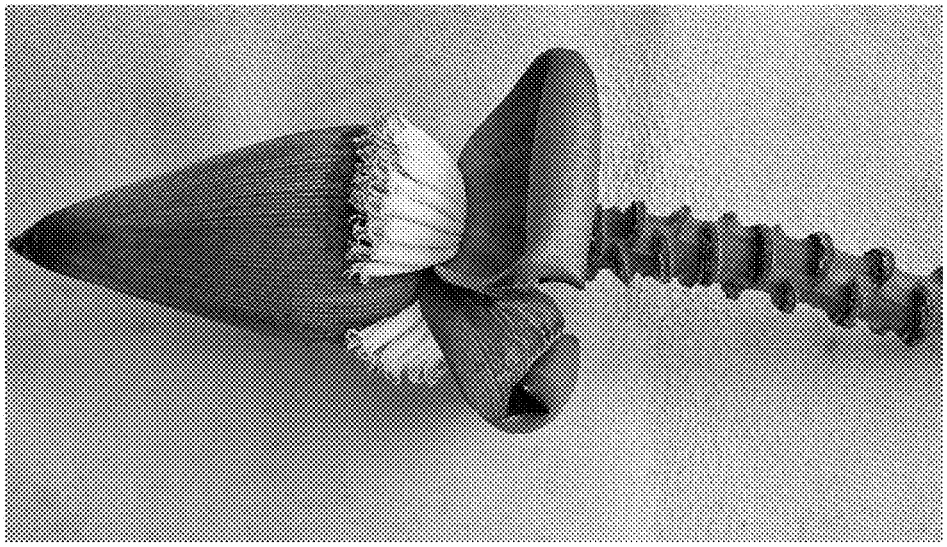
FIG. 6 shows a male bud.
Figures 9A, 9B:
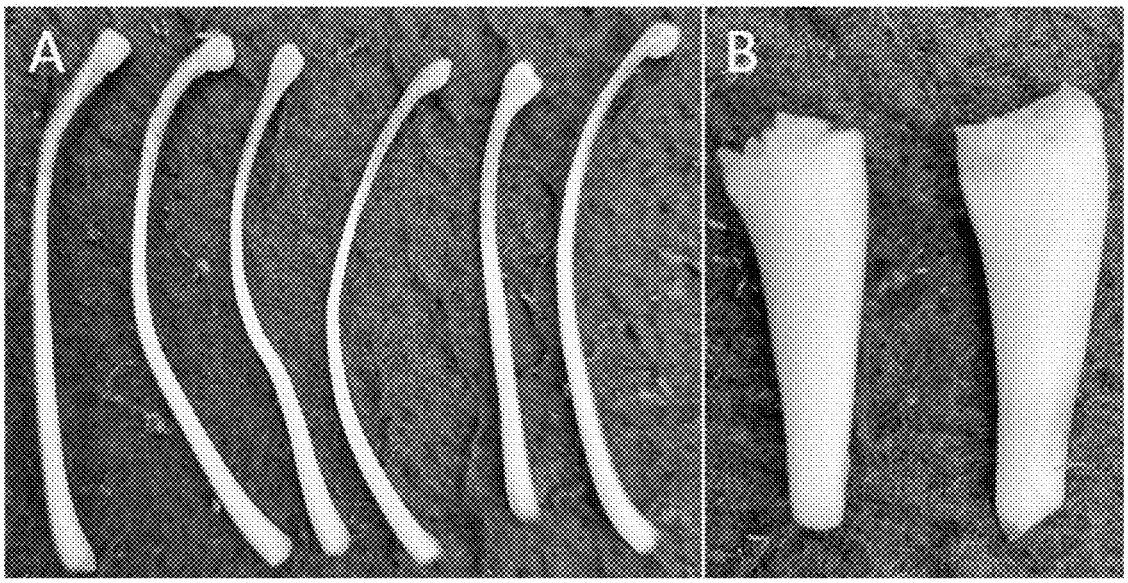
Figure 10:
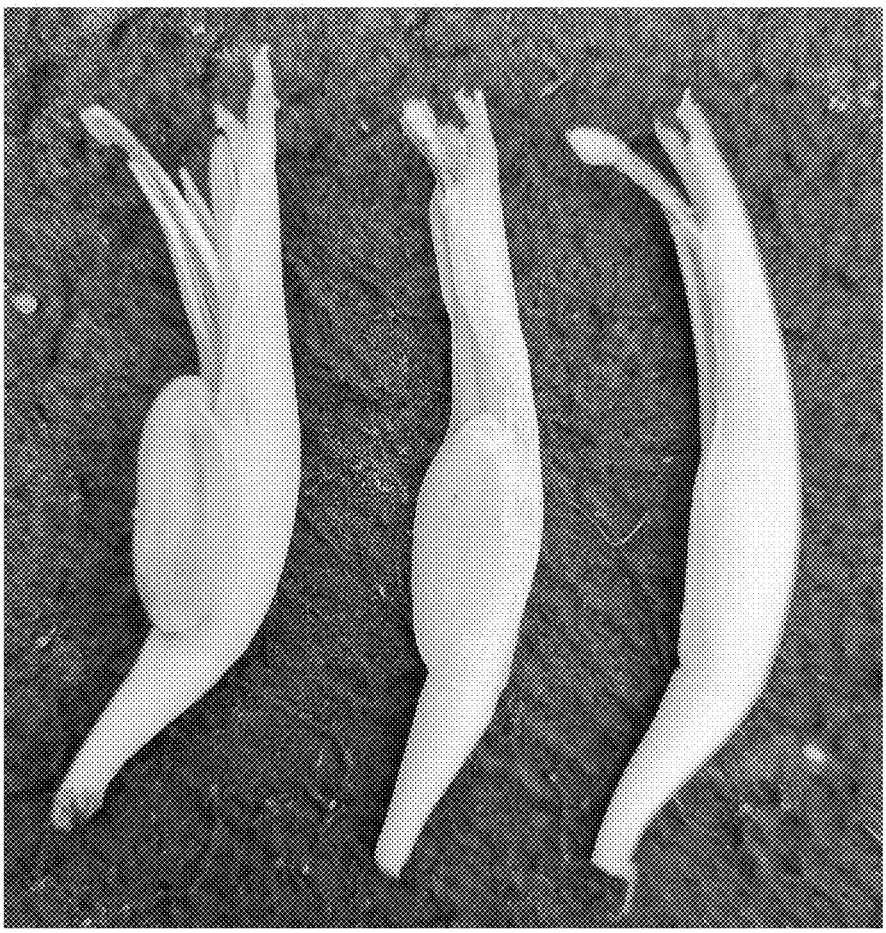
Figure 11:
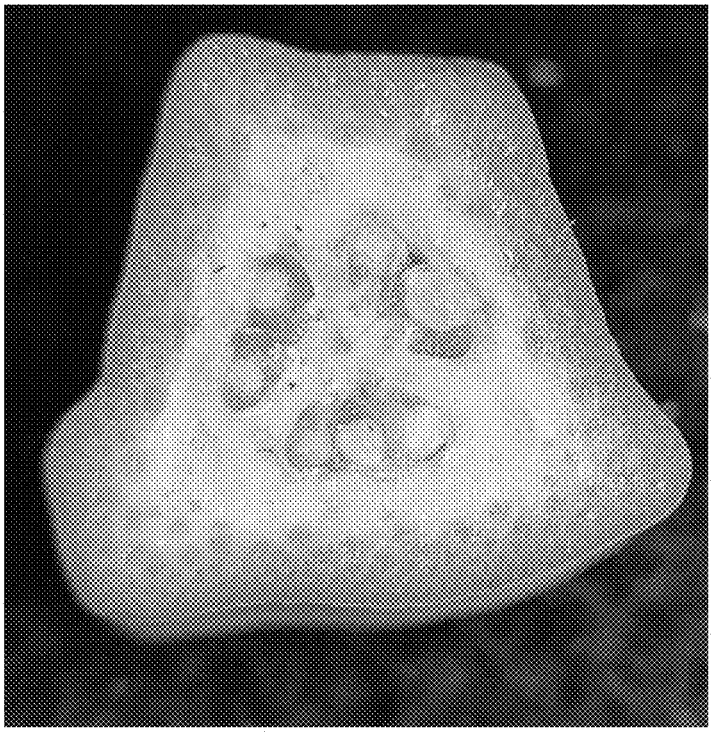

FIG. 7A-C shows bracts of male buds;

FIG. 8A-C shows compound tepals (A and B) and free tepals (C) lobes;

FIG. 9A-B shows the style shape (A) and an ovary (B);

FIG. 10 shows a male flower;

FIG. 11 shows rowed ovules; and

Figure 12:
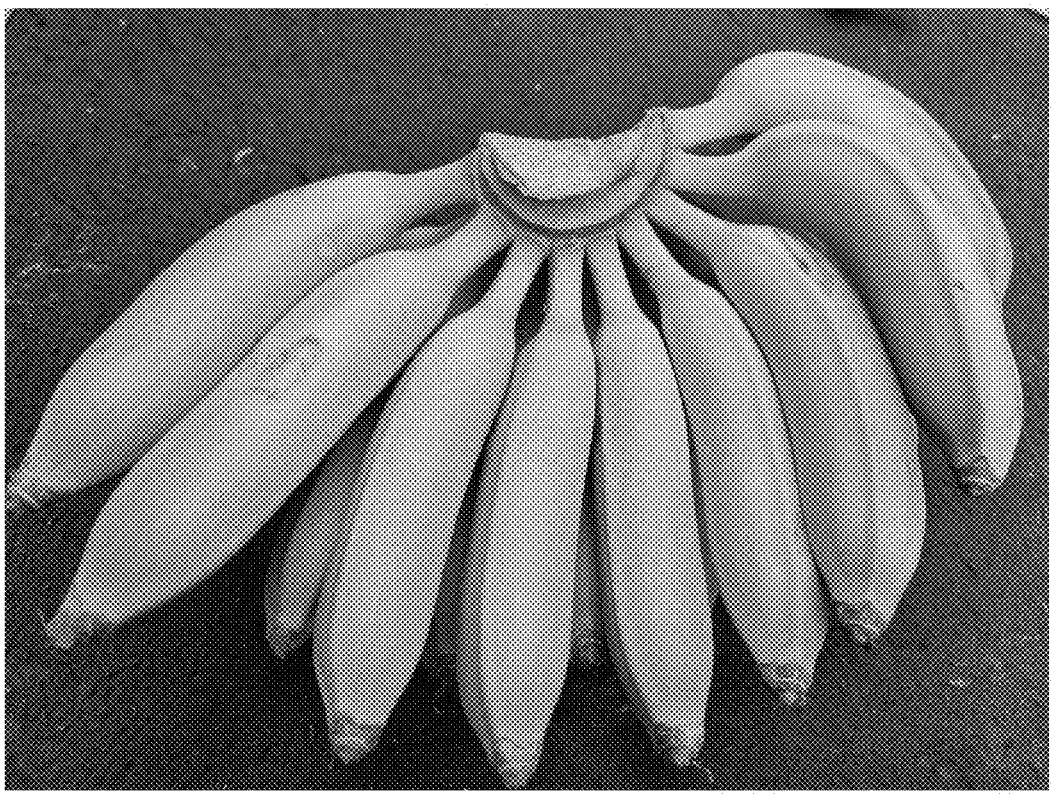

FIG. 12 shows a typical second hand.

DETAILED BOTANICAL DESCRIPTION

The following is a detailed botanical description of the new variety 'SH-4199'. The report is from plants located in La Lima, Cortés, Honduras that were evaluated in 2023. The descriptions concord with the internationally standardized "Descriptors for Banana (*Musa* spp.)" elaborated by IPGRI-INIBAP/CIRAD, 1996, and the U.K's Royal Horticultural Society's Colour Chart, 2001. The 'SH-4199' plant and its fruit may vary slightly from the detailed descriptors shown below due to cultural practices, soil types, and climatic conditions under which the variety may be cultivated.

| | |
|---|---|
| Leaf habit | Intermediate |
| Dwarfism | Dwarf type |
| Pseudostem length | 2.02 m |
| Pseudostem diameter | 67 cm |
| Pseudostem height | 2.1 to 2.9 meters |
| Pseudostem aspect | Robust |
| Pseudostem color | Yellow-Green (146D, RHS) |
| Pseudostem appearance | Shiny (Not waxy) |
| The predominant underlying color of the pseudostem | Greyed-red (179D, RHS) |
| Pigmentation of the underlying pseudostem | Greyed-Red (180A, RHS) |
| Sap color | Milky (4D, RHS) |
| Wax-on leaf sheaths | Very few waxes |
| Number of suckers | 3-4 |
| Development of suckers | >¼ and <¾ of the height of the parent plant |
| Position of suckers | Close to parent (vertical growth) |
| Blotches at the petiole base | Extensive pigmentation |
| Blotches color | Greyed-Brown (N199A, RHS) |
| Petiole canal leaf III | Straight with erect margins |
| Petiole margins | Winged and clasping the pseudostem |
| Wing type | Dry |
| Petiole margin color | Without color |
| Edge of petiole margin | Colourless (Without a color line along) |
| Petiole margin width | >1 cm |
| Leaf blade length | 221 to 260 cm |
| Leaf blade width | 81 to 90 cm |
| Petiole length | 51 to 70 cm |
| Color of the leaf's upper Surface | Green (136A, RHS) |
| Appearance of leaf upper surface | Dull |
| Color of the leaf's lower surface | Green (N138B, RHS) |
| The appearance of the leaf lower surface | Dull |
| Wax on leaves | Very wax |
| The insertion point of the leaf blade on the petiole | Asymmetric |
| The shape of the leaf blade base | One side is rounded, one-pointed. |
| Leaf corrugation | Very corrugated |
| Color of midrib dorsal surface | Green (141C, RHS) |
| Color of midrib ventral surface | Yellow-green (144B, RHS) |

-continued

| | |
|---|---|
| Color of cigar leaf dorsal surface | Green (139B, RHS) |
| Blotches on leaves of water suckers | Without blotches |
| Peduncle length | 61-70 cm |
| Empty nodes on the peduncle | Two or more |
| Peduncle width | 7-12 cm |
| Peduncle color | Green (136B, RHS) |
| Peduncle hairiness | Very hairy, short hairs (similar to velvet touch) |
| Bunch length | 66 cm |
| Bunch diameter | 77 cm |
| Number of hands per bunch | 12 |
| Bunch position | Hanging vertically |
| Bunch shape | Truncated cone shape |
| Bunch appearance | Very Compact |
| Flowers that form the fruit | Female |
| Fruits | Biseriate |
| Rachis type | Present and male buds may be degenerated or persistent |
| Rachis position | With a curve |
| Rachis appearance | Bare |
| Male bud type | Normal (present) |
| Male bud shape | Ovoid |
| Male bud size | 21 to 30 cm |
| Bract base shape | Large shoulder |
| Bract apex shape | Intermediate |
| Bract imbrication | Young bracts considerably overlap |
| Color of the bract external face | Purple (N79A, RHS) |
| Color of the bract internal ace | Greyed-Red (181A, RHS) |
| Color of the bract apex | Tinted with yellow (discolored) (17A, RHS) |
| Color stripes on the bract | Without discolored lines (not ridges)on the external face |
| Bract scars on rachis | Very prominent |
| Persistence of the bracts of the rachis | Moderate |
| Fading of color on bract base | Color homogenous |
| Male bract shape | Ovate |
| Male bract lifting | Lifting one at a time |
| Bract behavior before falling | Revolute (Rolling) |
| Wax on the bract | Moderately wax |
| Presence of grooves on the bract | Strongly grooved |
| Male flower behavior | Falling after the bract |
| Compound tepal basic color | White (155C, RHS) |
| Compound tepal pigmentation | Very few or no visible signs of pigmentation |
| Lobe color of compound tepal | Yellow-orange (17B, RHS) |
| Lobe development of compound tepal | Developed |
| Free tepal color | Translucent White (155D, HRS) |
| Free tepal shape | Oval |
| Free tepal appearance | Several folding under apex (corrugated) |
| Free tepal apex development | Developed |
| Free tepal apex shape | Triangular |
| Anther exertion | Inserted |
| Filament color | Yellow-Green (150D, RHS) |
| Anther color | Yellow-Green (150D, RHS) |
| Pollen sacs color | Yellow-Orange (16B, RHS) |
| Pollen vitality | Abundant |
| Style basic color | Yellow (4D, RHS) |
| Pigmentation on style | Without pigmentation |
| Style exertion | Inserted |
| Style shape | Straight |
| Stigma color | Yellow-Orange (17D, RHS) |
| Ovary shape | Arched |
| Ovary basic color | Yellow (4D, RHS) |
| Ovary pigmentation | Very few or no visible signs of pigmentation |
| The dominant color of male flower | White 155C, RHS) |
| Irregular flowers | Absent |
| Arrangement of ovules | Two rowed |
| Fruit position | Parallel to the stalk |
| Number of fruits | 17-21 |
| Fruit length | 16-20 cm |
| Fruit width | 2-3 cm |
| Fruit shape (longitudinal curvature) | Straight (or slightly curved) |

-continued

| | |
|---|---|
| Color of the flesh of the fruit | Creamy (8D, RHS) |
| Longitudinal ridges of the fruit | weak |
| Transverse section of fruit | Slightly ridged |
| Fruit apex | Bottle-necked |
| Remains of flower relicts at the fruit apex | Persistent style |
| Fruit pedicel length | 21-23 mm |
| Fruit pedicel width | 10-12 mm |
| Pedicel surface | Hairless |
| Fusion of pedicel | Very partially or no visible sign of fusion |
| Immature fruit peel color | Green (139C, RHS) |
| Mature fruit peel color | Yellow-orange (15B, RHS) |
| Fruit peel thickness | 1.5-2 mm |
| Adherence to the fruit peel | Fruit peels easily |
| Cracks in fruit peel | Without Cracks |
| Pulp in fruit | With pulp |

-continued

| | |
|---|---|
| Pulp color before maturity | White (155A, RHS) |
| Pulp color at maturity | White (155A, RHS) |
| Fruits fall from hands. | Persistent |
| Flesh texture | Firm |
| Predominant taste | Sweet |
| Presence of seed with the source of pollen | Without seeds |
| Seed surface | Without seeds |
| Seed shape | Without seeds |
| Growth habit of the plant | Upright |

The invention claimed is:

1. A new and distinct variety of banana plant named 'SH-4199', substantially as illustrated and described herein.

* * * * *

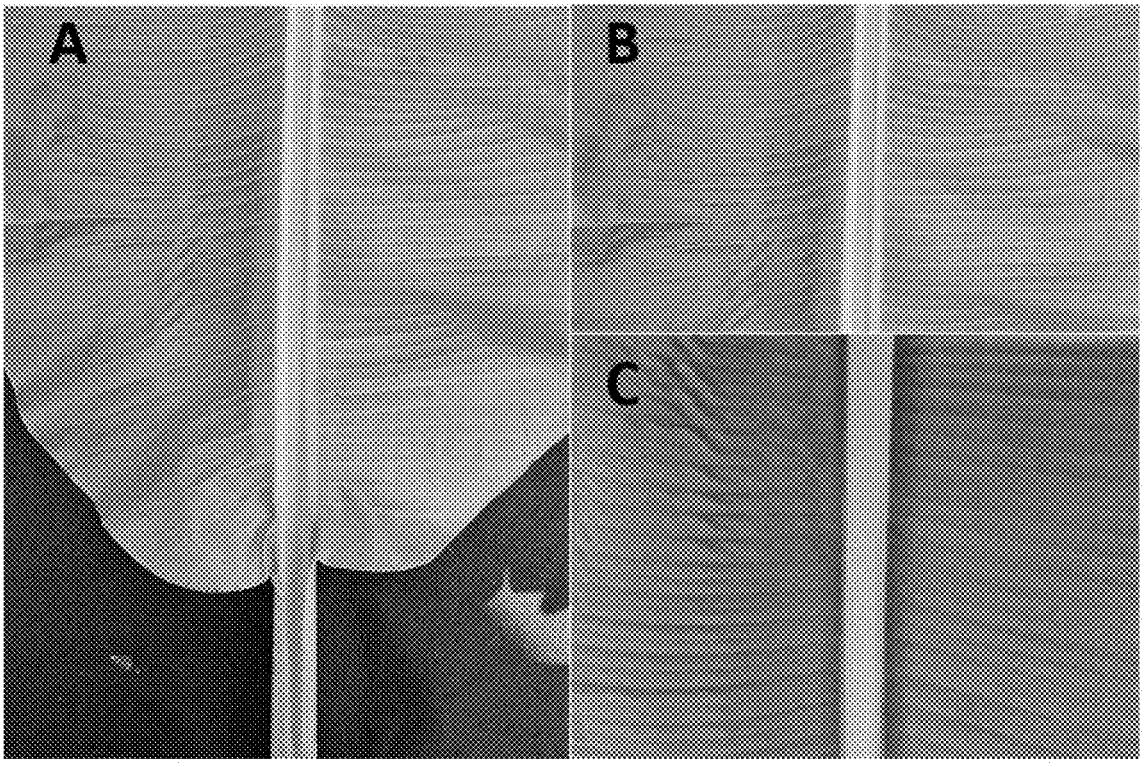
FIG. 3A, 3B, & 3C
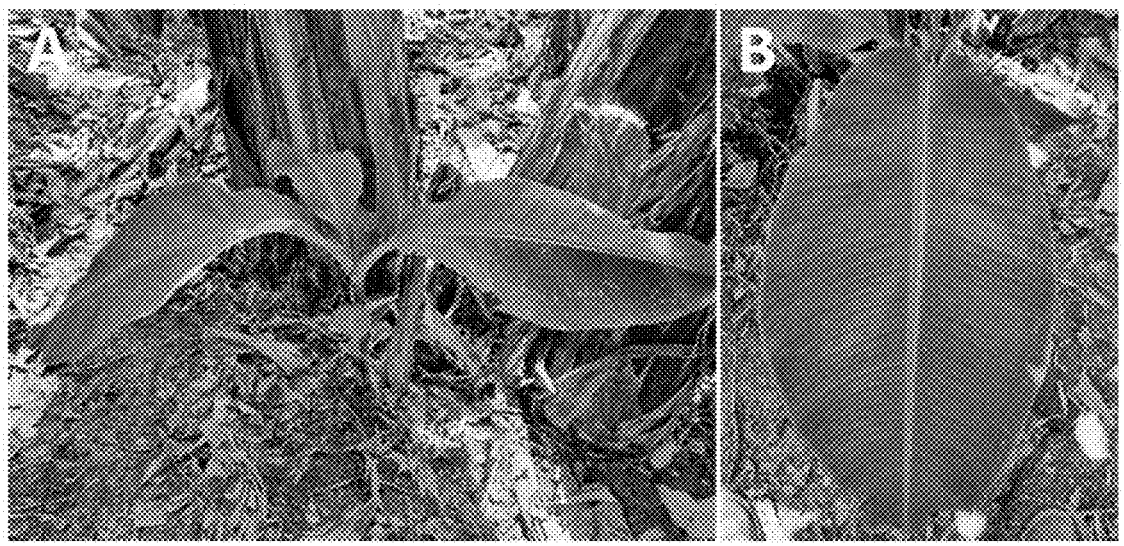
FIG. 4

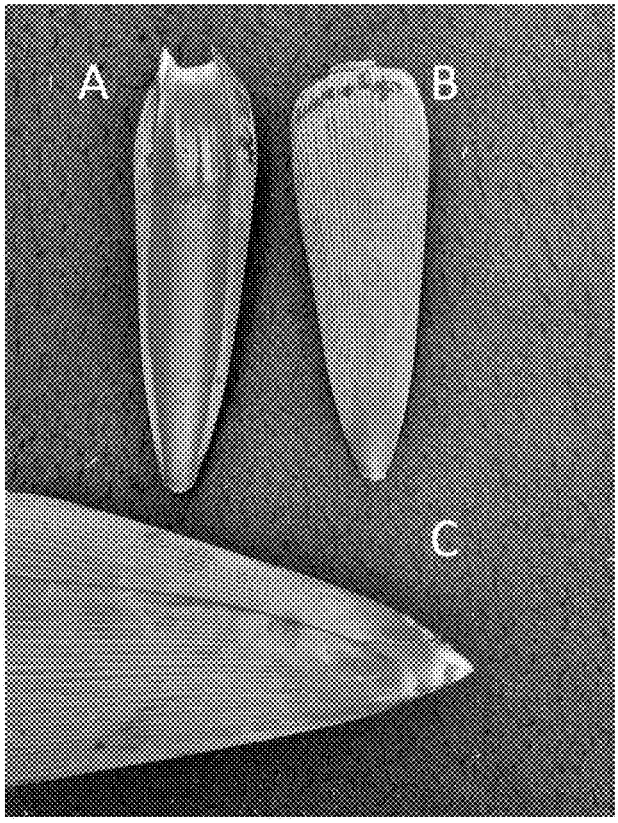
FIG. 7A, 7B, & 7C
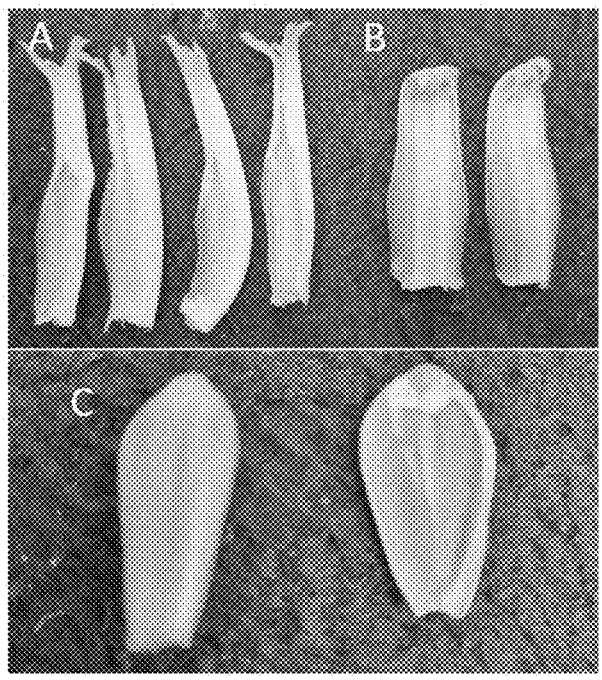
FIG. 8A, 8B, & 8C